United States Patent [19]

Lennox

[11] Patent Number: 5,507,824
[45] Date of Patent: Apr. 16, 1996

[54] ADJUSTABLE PROSTHETIC SOCKET COMPONENT, FOR ARTICULATING ANATOMICAL JOINTS

[76] Inventor: Dennis W. Lennox, 5003 Greenleaf Rd., Baltimore, Md. 21210

[21] Appl. No.: 24,206

[22] Filed: Feb. 23, 1993

[51] Int. Cl.$^6$ ........................................ A61F 2/34
[52] U.S. Cl. ............................... 623/22; 623/18
[58] Field of Search ................... 623/18, 19, 20, 623/22, 23

[56] References Cited

U.S. PATENT DOCUMENTS

| | | |
|---|---|---|
| Re. 28,895 | 7/1976 | Noiles . |
| 3,584,318 | 6/1971 | Scales et al. . |
| 3,903,549 | 9/1975 | Deyerle . |
| 3,996,625 | 12/1976 | Noiles . |
| 4,004,300 | 1/1977 | English . |
| 4,040,130 | 8/1977 | Laure . |
| 4,172,296 | 10/1979 | D'Errico . |
| 4,437,193 | 3/1984 | Oh . |
| 4,623,351 | 11/1986 | Church . |
| 4,623,352 | 11/1986 | Oh . |
| 4,642,123 | 2/1987 | Noiles . |
| 4,678,472 | 7/1987 | Noiles . |
| 4,681,589 | 7/1987 | Tronzo . |
| 4,743,262 | 5/1988 | Tronzo . |
| 4,792,337 | 12/1988 | Müller . |
| 4,883,490 | 11/1989 | Oh . |
| 4,904,265 | 2/1990 | MacCollum et al. . |
| 5,002,577 | 3/1991 | Bolesky et al. . |
| 5,041,140 | 8/1991 | Teinturier . |
| 5,074,881 | 12/1991 | Thull et al. . |
| 5,169,399 | 12/1992 | Ryland et al. . |
| 5,171,243 | 12/1992 | Kashuba et al. . |
| 5,171,285 | 12/1992 | Broderick . |
| 5,176,711 | 1/1993 | Grimes . |
| 5,192,329 | 3/1993 | Christie et al. . |

FOREIGN PATENT DOCUMENTS

| | | |
|---|---|---|
| 0091315 | 10/1983 | European Pat. Off. . |
| 2845231 | 5/1979 | Germany . |
| 2903366 | 8/1979 | Germany . |
| 2007980 | 5/1979 | United Kingdom . |
| 2029230 | 3/1980 | United Kingdom . |
| 2139098 | 5/1983 | United Kingdom . |
| 2117646 | 10/1983 | United Kingdom . |

OTHER PUBLICATIONS

Leadership through Design, The S–ROM™ Modular System, Joint Medical Products Corp., 1986.
It's as clear as black and white, DePuy Inc., 1992.
Simple to Use . . . The Wright Choice Total Hip System, Dow Corning Wright, 1992.
Simple to Choose!, Dow Corning Wright, 1992.

(List continued on next page.)

Primary Examiner—David Isabella

[57] ABSTRACT

A prosthetic socket component for articulating anatomical joints includes a shell member for being affixed to a first bone of the joint and a liner to be received in a cavity of the shell member through an opening in the shell member communicating with the cavity. The cavity has a longitudinal axis that is angularly offset from a longitudinal axis of the shell member, and the liner is rotatable relative to the shell member about the cavity axis to change the size of an angle made by a socket opening in the liner with the cavity opening. A method of implanting a prosthetic socket component includes the step of aligning a portion of the liner with one of a plurality of portions of the shell member to position the socket opening a predetermined angular distance from the cavity opening. An introducer for the prosthetic socket component includes a handle and a head for being received in the cavity with a longitudinal axis of the handle aligned with the shell member longitudinal axis. A system for implanting a prosthetic socket component includes the shell member, the introducer and the liner with the liner being mounted for rotation relative to the shell member to change the magnitude of the socket opening angle.

28 Claims, 3 Drawing Sheets

OTHER PUBLICATIONS

25 Years of Proven Clinical Success . . . The Textured Elite™ Modular Hip System, DePuy Inc., 1992 Put a cap on MicroMotion, C–2 OsteoCap™ Hip, Kirschner Medical Corporation.

Kirschner Products Have Built a Reputation by Helping Surgeons Build Theirs, Kirscher Med. Corp., 1992.

One precise system . . . for a not so precise population, Dow Corning Wright, 1992.

The old shell game . . . will never be the same, DePuy, 1991.

We're Smith & Nephew Richards. We are Orthopaedics, Smith & Nephew Richards Inc.

Decreasing Acetabular Wear, Contemporary Orthopaedics, Sep. 1992, vol. 25, No. 3.

Oblong cups for acetabular defects, The S–ROM™ total hip system, Joint Medical Products Corporation.

The unique solution . . . to difficult fracture management, C.M.W. Laboratories Ltd.

S–ROM™ Total Hip System, Joint Medical Products Corporation, 1988.

ABG cement free hip system, Howmedica International.

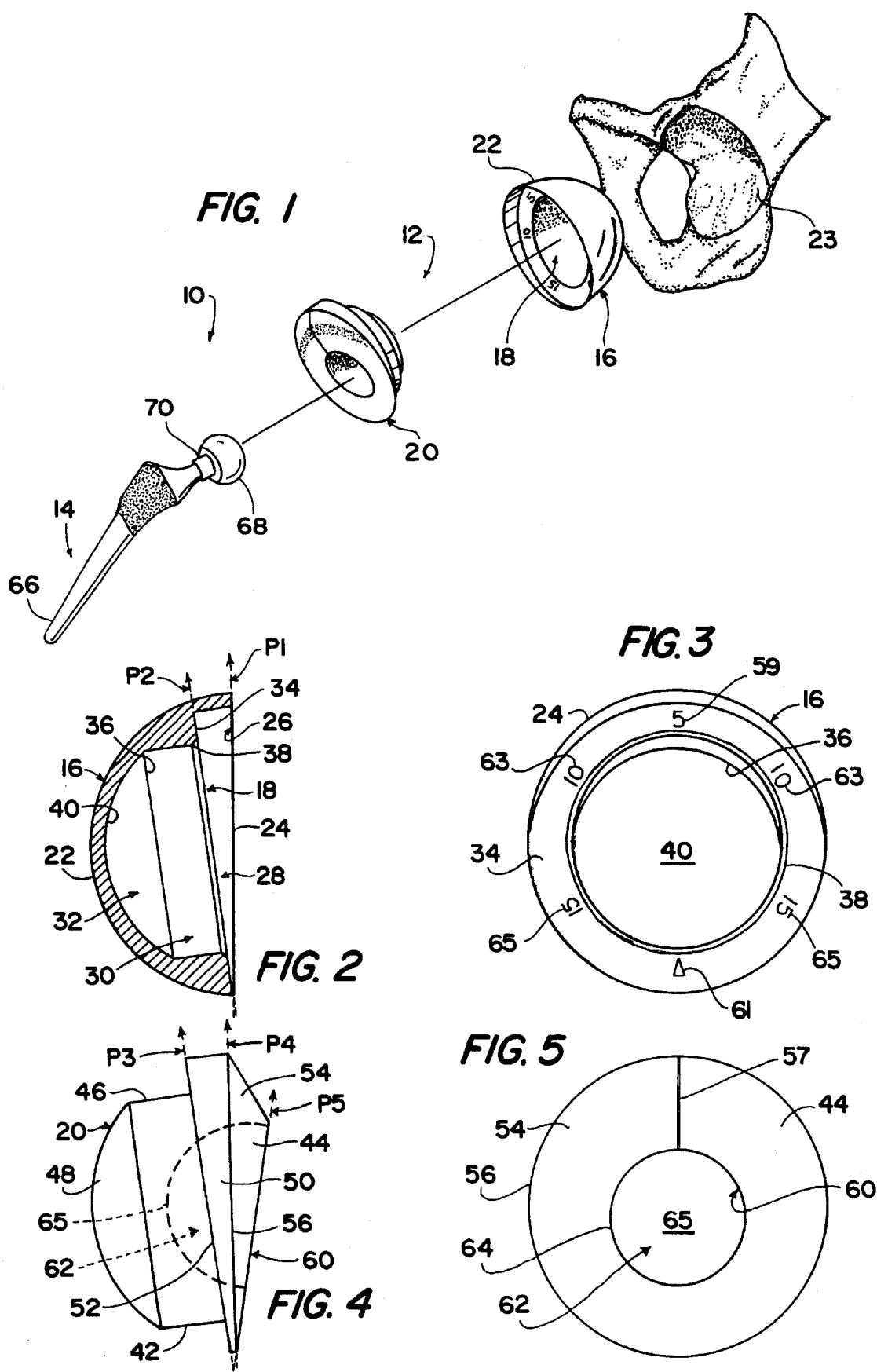

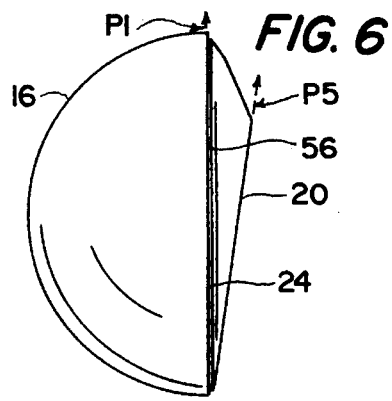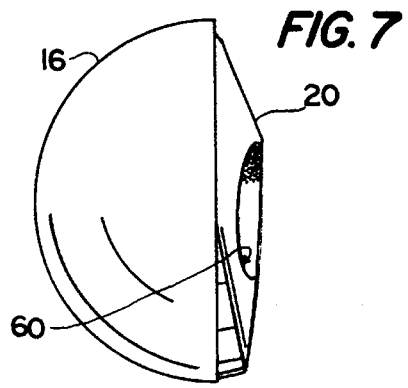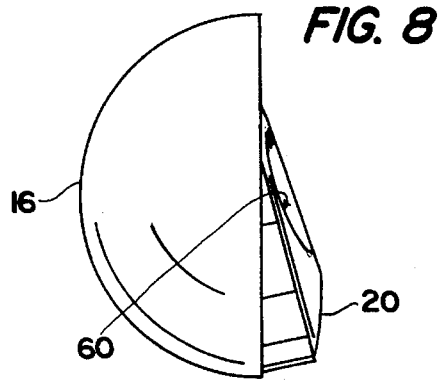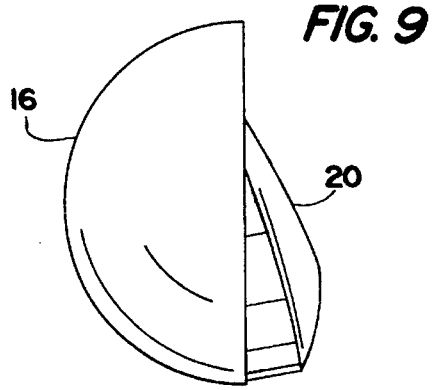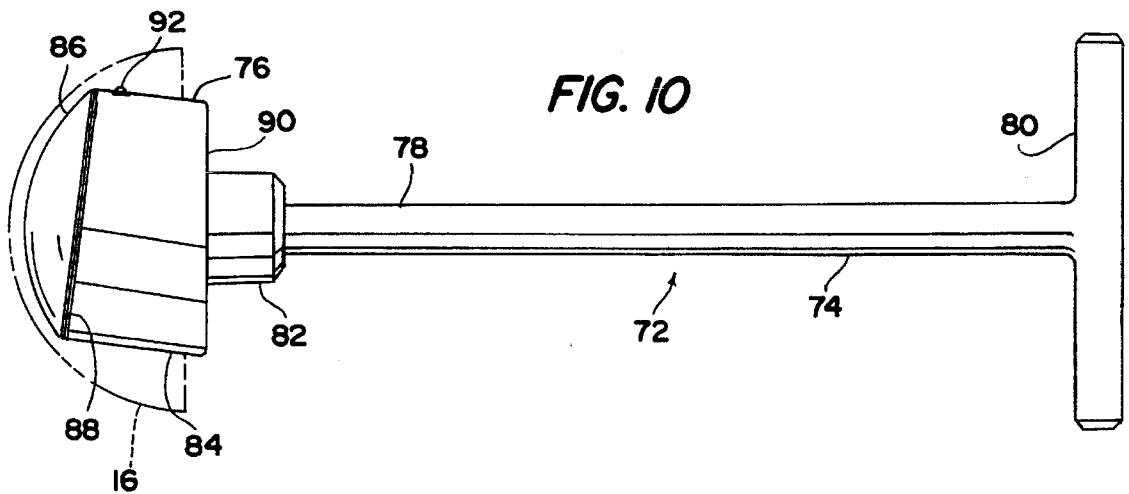

ADJUSTABLE PROSTHETIC SOCKET COMPONENT, FOR ARTICULATING ANATOMICAL JOINTS

BACKGROUND OF THE INVENTION

1. Field of the Invention

The present invention relates to joint surgery and, more particularly, to prosthetic socket components having socket openings that are adjustably positionable relative to ball components of the joints, introducers for positioning shells of prosthetic socket components on bones of the joints and systems and methods for use in joint surgery.

2. Description of the Prior Art

Various articulating joints of the body, such as the joints of the hips, have anatomical ball and socket connections between bones of the joints providing a wide range of motion. The hip joint, for instance, includes a socket or acetabulum in the pelvis and a femoral head or ball at an upper end of the femur or thigh bone received in the acetabulum. Where natural articulating joints are congenitally defective or become degraded due to disease or injury, prosthetic or artificial ball and socket components are commonly implanted in the body to replace the natural ball and socket structure of the joints. In total joint replacement surgery, prosthetic ball and socket components are both implanted as, for example, in total hip arthroplasty wherein a femoral stem component having a head or ball thereon to replace the natural femoral head is affixed to the femur, and a socket or acetabular component having a shell and a bearing insert or liner received in a cavity of the shell is affixed to the acetabulum with the head or ball of the femoral component rotatably or movably received in a socket of the liner to recreate the natural articulation of the hip joint. In subtotal or partial joint replacement surgery, natural bone structure of the joint is left intact to cooperate with an implanted prosthetic component, one example of subtotal joint replacement surgery being a cup arthroplasty wherein a prosthetic acetabular or socket component is implanted on the acetabulum to receive the natural femoral head. It is extremely important in total or partial joint replacement surgery and, in particular, total and subtotal hip replacement surgery, that the ball and socket components be optimally positioned in accordance with the physiological and anatomical features of the patient to ensure implant stability, resist dislocation and subluxation of the joint, enhance range of motion and avoid loosening or failure of the components. Accordingly, the liners of prosthetic acetabular components employed in hip surgery have been designed to protrude beyond openings to the cavities of the shells to angularly position the sockets of the liners to provide optimal coverage of the prosthetic femoral heads by the socket components to resist dislocation. U.S. Pat. Nos. 5,171,285 to Broderick, 5,169,399 to Ryland et al, 5,002,577 to Bolesky et al, 4,883,490, 4,623,352 and 4,437,193 to Oh, 4,792,337 to Müller, 4,678,472 to Noiles and 4,623,351 and United Kingdom patent 2 117 646 to Church are illustrative of acetabular components including liners having socket openings therein and shells or cups having cavities therein with openings for receiving the liners with portions of the liners angularly protruding beyond the planes of the cavity openings to angularly position the socket openings to receive a head or ball. The portions of the liners protruding beyond the planes of the cavity openings define angularly protruding lips or overhangs and, in some prosthetic socket components, the liners can be rotated relative to the shells about axes perpendicular to the planes of the cavity openings to change the position of the lips or overhangs to inhibit dislocation.

A major disadvantage of prior prosthetic socket components is that the angular distance that the liners protrude beyond the planes of the cavity openings is fixed or constant for a specified liner such that only a single size or angle of overhang can be obtained with an individual liner. Accordingly, only one size or magnitude of angle for the socket opening can be obtained with a particular liner, the angle obtained being dependent on the angle that the protruding portion of the liner defines with the plane of the cavity opening. Because the most advantageous angle for the socket opening can vary greatly among individual patients in accordance with anatomical and physiological features as determined during joint surgery, many diverse liners with different sizes or angles of overhang must typically be available during joint surgery for use as trial liners to allow a surgeon to select the best size or angle of overhang and, therefore, optimal socket opening angle, for the patient. In addition to the various trial liners, liners intended for final implantation and corresponding to the trial liners must also be available to the surgeon during joint surgery thusly necessitating a very large and costly inventory of components. Another disadvantage of prior prosthetic socket components is that the process of inserting a different trial liner in the shell for each size or angle of overhang to be considered for the patient can be tedious and time consuming and greatly impairs intraoperative flexibility. Prior prosthetic socket components have a further disadvantage in that positioning of the overhangs to resist dislocation does not produce anteversion or retroversion of the liners for increased range of motion.

SUMMARY OF THE INVENTION

Accordingly, it is a primary object of the present invention to overcome the above-mentioned disadvantages of prior art prosthetic socket components.

Another object of the present invention is to provide a prosthetic socket component having a liner that is adjustable relative to a shell member receiving the liner to change the angular distance that a portion of the liner protrudes beyond the shell member.

A further object of the present invention is to provide a prosthetic socket component having one liner that is adjustable relative to a shell member receiving the liner to obtain various sizes or magnitudes of angles for a socket opening of the liner.

Still another object of the present invention is to provide a prosthetic socket component having a liner that is adjustable relative to a shell member receiving the liner to vary the size of a portion of the liner that protrudes beyond the shell member.

An additional object of the present invention is to provide a prosthetic socket component having a liner that is adjustable relative to a shell member receiving the liner between a neutral position wherein the liner does not protrude or protrudes a predetermined minimum amount from the shell member and an extreme position wherein the liner protrudes a predetermined maximum amount from the shell member.

It is also an object of the present invention to provide a prosthetic socket component having a liner that is adjustable relative to a shell member receiving the liner to increase anteversion or retroversion of the liner in response to movement of the liner to change the angle of a socket opening in the liner.

The present invention has as a further object to provide a prosthetic socket component having a shell member with indicia markings thereon and a liner for being received in the shell member with a reference mark thereon alignable with one of the indicia markings to obtain one of a plurality of predetermined angles for a socket opening of the liner.

Another object of the present invention is to provide a prosthetic socket component having a shell member with indicia markings thereon corresponding to different sizes or magnitudes of angles for a socket opening of a liner received in a cavity of the shell member, with a reference mark on the liner alignable with a selected one of the indicia markings to obtain an angle for the socket opening corresponding to the selected indicia marking.

A still further object of the present invention is to provide a prosthetic socket component having a liner received in an opening of a cavity of a shell member with the liner being rotatable relative to the shell member about an axis that is non-perpendicular or non-orthogonal to the plane of the cavity opening to change the size of an angle that a socket opening of the liner defines with the plane of the cavity opening.

Yet another object of the present invention is to provide an introducer for inserting a prosthetic socket component on a bone and having a handle and a head joined to the handle, the head having a longitudinal axis angularly offset from a longitudinal axis of the handle to permit the socket component to be mounted on the head with the handle longitudinal axis aligned with a longitudinal axis of the socket component.

An additional object of the present invention is to provide a method of implanting a prosthetic socket component in joint surgery including the step of aligning a portion of a liner of a prosthetic socket component with one of a plurality of portions of a shell of the prosthetic socket component to position a socket opening in the liner a predetermined angular distance from a cavity opening in the shell receiving the liner.

Another object of the present invention is to provide a system for implanting a prosthetic socket component during joint surgery including a shell member, an introducer and a liner, the liner being mounted for rotation relative to the shell member to change the magnitude of an angle made by a socket opening of the liner with a cavity opening of the shell member.

Some of the advantages of the present invention are that inventories of liners for prosthetic socket components utilized during joint surgery can be greatly reduced, i.e. by at least ⅔, the need for trial components can be greatly reduced or eliminated, customization of prosthetic socket components and maximum joint stability can be obtained via adjustment of a single liner, the range of motion for prosthetic joints can be enhanced via anteversion or retroversion of the liner, a safety feature can be provided by designing the liner to protrude beyond the plane of the cavity opening in the neutral position, dislocation and subluxation of articulating joints can be avoided, intraoperative flexibility during joint surgery is increased, Joint replacement surgery is facilitated and prosthetic socket components according to the present invention can be made utilizing conventional materials and manufacturing processes, resemble conventional prosthetic socket components in an assembled condition and are compatible with well known surgical techniques.

These and other objects, advantages and benefits are obtained with the present invention as characterized in a prosthetic socket component for articulating Joints including a shell member for being affixed to a first bone of the joint and a liner to be received in a cavity of the shell member. The shell member includes an outer surface terminating at a forward edge or rim circumscribing an opening to the cavity, and the cavity opening is contained in a plane perpendicular to a longitudinal axis of the shell member. The cavity includes a forward cavity section, an intermediate cavity section and an end cavity section with a longitudinal axis angularly offset from the longitudinal axis of the shell member. The forward cavity section extends lengthwise from the rim to a platform in the shell member, and the platform is contained in a plane disposed at an angle with the plane of the cavity opening that is the same as the angle that the cavity axis is offset from the shell member axis. The forward cavity section is tapered about the cavity axis to have a maximum length where the angular distance between the plane of the cavity opening and the plane of the platform is greatest and a minimum length where the angular distance between the plane of the cavity opening and the plane of the platform is smallest. The liner has a mounting end to be received in the intermediate and end cavity sections and a hood with a rear portion to be received in the forward cavity section. The rear portion of the hood is complementary in configuration to the forward cavity section and is tapered about a longitudinal axis of the liner to have a maximum thickness corresponding to the maximum length of the forward cavity section and a minimum thickness corresponding to the minimum length thereof. A socket in the liner has an opening in the hood for receiving a ball component secured to a second bone of the joint. With the mounting end of the liner received in the intermediate and end cavity sections of the shell member, the socket opening is contained in a plane disposed at an angle with the plane of the cavity opening. The liner is rotatable relative to the shell member about the cavity axis to change the size or magnitude of the angle between the plane of the socket opening and the plane of the cavity opening to resist dislocation. An introducer in accordance with the present invention includes a handle having a longitudinal axis and a head for being received in the cavity of the shell member with the handle axis aligned with the longitudinal axis of the shell member. A method of implanting a prosthetic socket component in joint surgery according to the present invention includes the step of aligning a portion of the liner with one of a plurality of portions of the shell member to position the socket opening a predetermined angular distance from the cavity opening corresponding to the portion of the shell member with which the liner portion is aligned. According to the present invention, a system for implanting a prosthetic socket component during joint surgery includes the shell member, the introducer and the liner with the liner being mounted for rotation relative to the shell member to change the magnitude of the angle defined by the socket opening with the cavity opening.

Other objects and advantages of the present invention will become apparent from the following description of the preferred embodiments taken in conjunction with the accompanying drawings wherein like parts in each of the several figures are identified by the same reference characters. dr

BRIEF DESCRIPTION OF THE DRAWINGS

FIG. 1 is an exploded perspective view of a prosthetic hip joint including an adjustable socket component in accordance with the present invention.

FIG. 2 is a side sectional view of the shell member of the socket component of FIG. 1.

FIG. 3 is a front view of the shell member of FIG. 2.

FIG. 4 is a side view of the liner of the socket component of FIG. 1.

FIG. 5 is a front view of the liner of FIG. 4.

FIG. 6 is a side view of the socket component of FIG. 1 in an assembled condition with the liner in a neutral position.

FIG. 7 is a side view of the socket component of FIG. 1 in the assembled condition with the liner in a first intermediate position.

FIG. 8 is a side view of the socket component of FIG. 1 in the assembled condition with the liner in a second intermediate position.

FIG. 9 is a side view of the socket component of FIG. 1 in the assembled condition with the liner in an extreme position.

FIG. 10 is a side view of an introducer tool for the socket component of FIG. 1.

DESCRIPTION OF THE PREFERRED EMBODIMENTS

Figure 11:
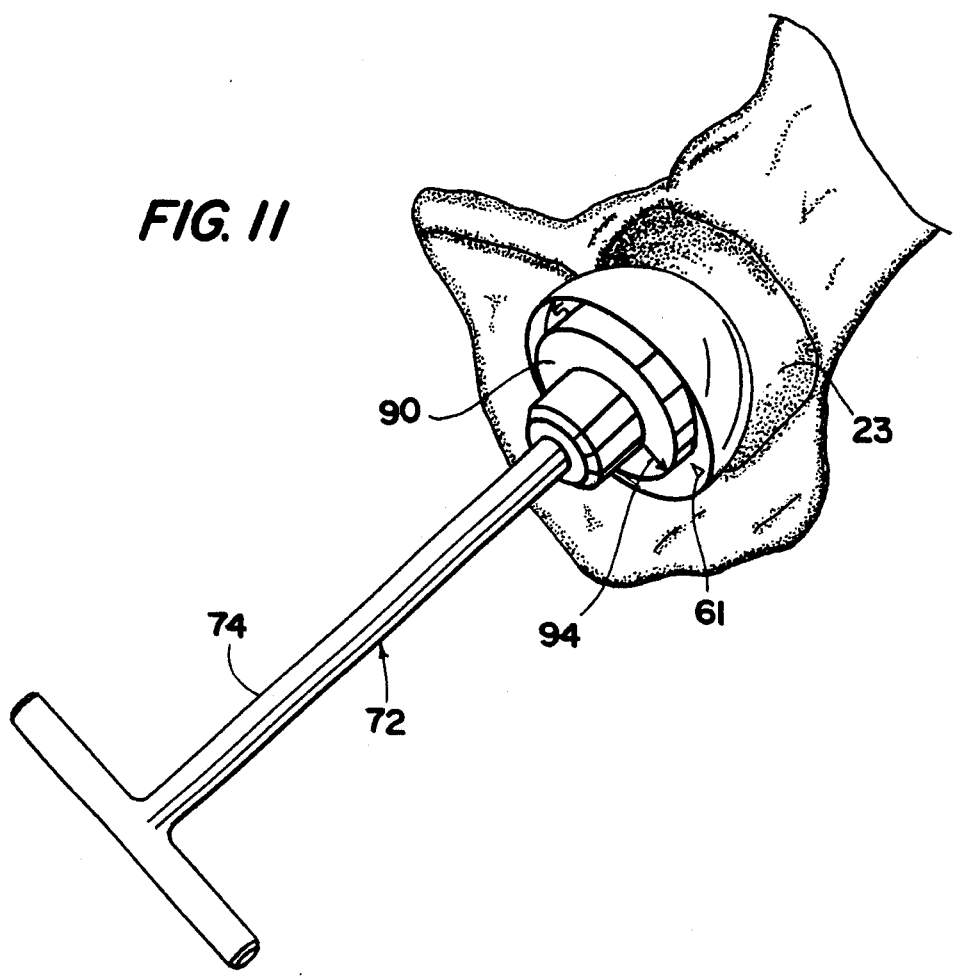
FIG. 11 is a perspective view of the introducer of FIG. 10 being utilized to insert the shell member of FIG. 2 in an acetabular recess.

A prosthetic articulating joint 10 made up of a socket component or assembly 12 according to the present invention and a stem component 14 is illustrated in FIG. 1. Prosthetic joint 10 is designed to be implanted in the body to replace a natural articulating joint with socket component 12 and stem component 14 affixed to respective bones of the joint. Socket component or assembly 12 includes a shell member 16 having a cavity 18 therein and a bearing insert or liner 20 to be received in cavity 18. Shell member 16 is preferably made of a medical grade material, including metals such as titanium and cobalt chrome, suitable for implantation in the body and has an outer or external configuration or contour selected in accordance with the bone in the body to which the socket component 12 is to be affixed. Prosthetic joint 10 illustrated in FIG. 1 is designed to replace the natural hip joint; and, accordingly, shell 16 has a curved, hemispherical or partial spherical outer surface 22 for being implanted on a prepared surface or recess 23 of the acetabulum. Shell member 16 can be affixed in many various ways including a press fit, bone ingrowth processes, cementing, impaction, mechanical fixation devices such as screws or a combination thereof. If desired, all or a portion of outer surface 22 can be textured, irregular or made porous or with many small interstices or beads to facilitate bone ingrowth processes. Outer surface 22 can have various configurations including oblong or elliptical as well as various sizes dependent on the size and configuration of the acetabular recess and, by providing shell member 16 in various diverse sizes and configurations, a shell member best suited to the anatomical and physiological characteristics of the patient can be selected. According to one embodiment, outer surface 22 is hemispherical in configuration with a radius of approximately 1.260 inches; however, where it is desired to provide shell member 16 with a low or reduced profile, outer surface 22 can be less than a hemisphere. As illustrated in FIGS. 2 and 3, outer surface 22 terminates at a circular forward edge or rim 24 disposed in a plane P1 perpendicular to a central longitudinal axis of the shell member. The shell member longitudinal axis is coincident or aligned with a center line of the outer diameter of the shell member along rim 24 and with a longitudinal axis of the socket component 12. Where outer surface 22 is a hemisphere, the radius for outer surface 22 is defined from a point along the shell member longitudinal axis and disposed in plane P1. Where outer surface 22 is less than a hemisphere, the radius for outer surface 22 is defined from a point along the shell member longitudinal axis but disposed forwardly, i.e. to the right in FIG. 2, of plane P1, and the distance that this point is disposed forwardly of plane P1 can vary in accordance with the profile desired for shell member 16, one preferred distance being 0.125 inches. Rim 24 circumscribes or surrounds an opening 26 of cavity 18, the opening 26 being disposed in plane P1. Cavity 18 has a configuration to receive liner 20 and a longitudinal axis angularly offset from the longitudinal axis of shell member 16. As best illustrated in FIG. 2, cavity 18 includes a forward cavity section 28, an intermediate cavity section 30 and an end cavity section 32. Forward cavity section 28 is generally circular in cross-section and extends longitudinally, or lengthwise, from opening 26 to an annular platform or surface 34 contained in a plane P2 angularly disposed with plane P1. Plane P2 is perpendicular to the cavity axis, and the angle defined between planes P1 and P2 is the same as the angle that the cavity axis is offset from the longitudinal axis of the shell member. According to a preferred embodiment, the angle between planes P1 and P2 is 7½°. Accordingly, the length of forward section 28 between planes P1 and P2 about the cavity axis from a maximum length where the angular distance between planes P1 and P2 is greatest to a minimum length where the angular distance between plane P1 and plane P2 is smallest with the maximum and minimum lengths being diametrically opposed to one another or spaced 180°. Depending on the configuration of shell member 16, forward edge or rim 24 can merge with platform 34 at the location of minimum length such that planes P1 and P2 intersect as shown in FIG. 2 or the rim 24 and, therefore, plane P1, can be spaced forwardly of plane P2 and platform 34 at the location of minimum length. Intermediate cavity section 30 is circular in cross-section and cylindrical and extends longitudinally from platform 34 to a circular junction 36 joining the intermediate cavity section to end cavity section 32. If desired, the innermost edge 38 of platform 34 can be bevelled or angled to provide a smooth transition between forward cavity section 28 and intermediate cavity section 30. End cavity section 32 is curved, hemispherical or partial spherical in configuration to define an end wall 40 corresponding to or congruent with outer surface 22, and the end cavity section 32 merges with intermediate cavity section 30 at junction 36.

Bearing insert or liner 20 is desirably made as one piece of a medical grade material, including synthetic or plastic materials such as polyethylene, preferably having high strength, low friction and high lubricity characteristics and includes a body having a nose or mounting end 42 and a hood 44. Nose 42 has a size and configuration to be received in cavity 18 of shell member 16 and, as illustrated in FIG. 4, is made up of a cylindrical segment 46 extending longitudinally from hood 44 in a rearward direction and a partial spherical segment 48 rearwardly joined to cylindrical segment 46. Cylindrical segment 46 has an outer diameter and length to be closely received by intermediate cavity section 30, and partial spherical segment 48 is sized and configured to be closely received by end cavity section 32. Various types of locking mechanisms can be utilized with socket component 12 to retain liner 20 in engagement with shell member 16 and prevent removal of nose 42 from cavity 18. Some examples of suitable locking mechanisms include a friction or press fit, ring type locking devices such as O-rings positioned circumferentially to engage the wall of cavity 18 and barbed fittings. As shown in FIGS. 4 and 5, hood 44 includes a rear portion 50 having a circular, planar rear face or surface 52 from which nose 42 extends concentrically and a forward portion 54 joined to rear portion 50 at a circular rim 56. Rear face 52 is disposed in a plane P3 perpendicular to the longitudinal axis of the liner, and rim 56 is contained in a plane P4 disposed at an angle with plane P3 that is the same as the angle between planes P1 and P2. Rear portion 50 is tapered between rim 56 and rear face 52 to have from a maximum thickness where the angular distance between plane P4 and plane P3 is greatest and a minimum thickness where the angular distance between plane P4 and plane P3 is smallest, and the maximum and minimum thicknesses are diametrically opposed to one another or spaced 180°. Rear portion 50 has a circular cross-section along its thickness, with an outer diameter to fit within opening 26 of shell 16. With the angle between planes P3 and P4 being the same as the angle between planes P1 and P2, rear portion 50 has a configuration the same as or substantially the same as or corresponding to or complementary to the configuration of forward cavity section 28. A reference mark 57 can be provided on the liner 20, such as along forward portion 54, to visually indicate or identify the location of maximum thickness, and a first indicia marking 59 can be provided on shell member 16, such as on platform 34, to visually identify the location of maximum length for forward cavity section 28 to facilitate assembly of the liner on the shell member in a neutral position as will be explained further below. As illustrated in FIG. 5, reference mark 57 includes a line etched into the surface of forward portion 54 at the location of maximum thickness; and, as shown in FIG. 3, first indicia marking 59 includes a numeral on platform 34 at the location of maximum length. It is preferred that at least forward portion 54 of liner 20 could be made transparent or a window made in the liner to permit visualization of first indicia marking 59 therethrough to facilitate alignment of the maximum thickness with the maximum length when assembling the liner in the neutral position as will be explained further below. Forward portion 54 of hood 44 defines a forward face or surface 58 of liner 20 with a circular opening 60 therealong leading to a socket 62. Opening 60 is contained in a plane P5 angularly disposed with plane P4 of rim 56; and, according to the preferred embodiment, the angle that plane P5 defines with plane P4 is 5°. The first indicia marking 59 corresponds to the size of the angle between planes P5 and P4 to provide a visual indication of the angle that socket opening 60 defines with plane P1 in the neutral position as will be explained further below; and, as shown in FIG. 3, first indicia marking 59 includes the number "5" corresponding to the 5° angle. Forward face 58 merges with rear portion 50 at rim 56 and has an outwardly curved or convex configuration extending forwardly from rim 56 in the direction of the liner axis to terminate at an annular or circular edge 64 circumscribing or surrounding socket opening 60. The curvature of forward face 58 is non-uniform or non-constant about a longitudinal axis of socket 62 coincident with the center of socket opening 60 and perpendicular to plane P5 such that the forward face 58 has a maximum or more steep curvature where the angular distance between planes P4 and P5 is greatest and a minimum or more gentle or gradual curvature where the angular distance between planes P4 and P5 is smallest. The maximum and minimum curvatures are diametrically opposed to one another or spaced 180° with the maximum curvature aligned with the maximum thickness of rear portion 50 and the minimum curvature aligned with the minimum thickness of the rear portion. Socket 62 has a hemispherical or partial spherical configuration defining a concave bearing surface 65 for the head or ball of a stem component, such as stem component 14.

With liner 20 assembled on shell member 16, cylindrical segment 46 and partial spherical segment 48 of nose 42 will be closely received in intermediate and end cavity sections 30 and 32, respectively. Rear portion 50 of hood 44 will be received in forward cavity section 28 with rear face 52 in abutment with platform 34 and the longitudinal axis of cavity 18 aligned with the longitudinal axis of liner 20. With the reference mark 57 on the liner aligned with the first indicia marking 59 on the shell member, the liner will be in the neutral position with rear portion 50 substantially completing forward cavity section 28 and rim 56 or plane P4 of the liner aligned or substantially aligned with rim 24 or plane P1 of the shell member as illustrated in FIG. 6. In the neutral position, socket opening 60 is disposed at an angle with the plane P1 of the cavity opening 26 that is equal or substantially equal to the angle defined between the plane P4 of rim 56 and the plane P5 of the socket opening 60, i.e. 5° for the preferred embodiment. Accordingly, the forward portion 54 of hood 44 overhangs or protrudes angularly beyond the plane P1 of the cavity opening 26 a predetermined initial angular distance to position socket opening 60 at a predetermined initial angle with plane P1 corresponding to first indicia marking 59. It should be appreciated that liner 20 can be configured in many ways in accordance with the angle desired for the socket opening 60 in the neutral position and that the hood 44 can be flush or substantially flush with the cavity rim 24 such that no overhang is provided in the neutral position. The size or angle of the overhang, which is the portion of the liner protruding beyond the cavity opening 26, can be varied or changed to vary or change the angle that socket opening 60 defines with plane P1 by manually rotating or dialing the liner 20 relative to shell member 16 about the longitudinal axis of cavity 18, such axis being non-perpendicular or non-orthogonal to plane P1. The angle of the socket opening 60, which is the angle between planes P5 and P1, can be adjusted from a minimum angle corresponding to the neutral position to a maximum size or angle corresponding to an extreme position illustrated in FIG. 9. In the extreme position, the maximum thickness of rear portion 50 is aligned with the minimum length of forward cavity section 28; and, accordingly, the extreme position is obtained by rotating the liner 180°. A second indicia marking 61 corresponding to the angle of the socket opening 60 with plane P1 in the extreme position can be provided on platform 34 at the location of minimum length to facilitate alignment of the maximum thickness and minimum length via alignment of reference mark 57 with second indicia marking 61. Second indicia marking 61 can be a numeral corresponding to the magnitude or size of the angle for the socket opening 60 in the extreme position, i.e. 20° for the preferred embodiment, or the second indicia marking 61 can be an arrow as illustrated in FIG. 3 with the arrow pointing in the direction of the longitudinal axis of cavity 18 to facilitate assembly of shell 16 on an introducer tool as will be explained further below. In the extreme position, the minimum thickness of rear portion 50 will be aligned with the maximum length of forward cavity section 28 with rim 56 bisecting plane P1 of rim 24 causing a part of forward portion 54 directly opposite, diametrically opposed to or 180° from the maximum thickness to be moved into forward cavity section 28 rearwardly of plane P1. Various intermediate sizes of angles for the socket opening 60 can be obtained between the neutral and extreme positions, the size of socket opening angle obtained increasing as the liner 20 is rotated or dialed from the neutral position toward the extreme position. From the neutral position, the liner 20 can be rotated clockwise or counterclockwise toward the extreme position, and the size or angle obtained for a specified amount of rotation from the neutral position will be the same in the clockwise and counterclockwise directions. First and second pairs of intermediate indicia markings 63 and 65 can be provided along platform 34 for alignment with reference mark 57 in first and second intermediate positions, the markings of each pair being provided along platform 34 at corresponding angular locations in clockwise and counterclockwise directions from the neutral position. Indicia markings 63 are illustrated in FIG. 3 as numerals corresponding to the angle of socket opening 60 with plane P1 when reference mark 57 is aligned therewith via rotation of liner 20 clockwise or counterclockwise, i.e. right or left. The first intermediate positions, as indicated by markings 63, are located approximately 60° from the neutral position for the preferred embodiment to obtain an angle for the socket opening of 10°. Indicia markings 65 are illustrated as numerals corresponding to the angle of socket opening 60 with plane P1 when reference mark 57 is aligned therewith in second intermediate positions located approximately 120° from the neutral position, the angle being 15° for the preferred embodiment. In the first and second intermediate clockwise positions illustrated in FIGS. 7 and 8, respectively, portions of the liner 20 opposite the maximum thickness are received in cavity 18, and the size of the part or portion of liner 20 that is received in cavity 18 increases as the liner is dialed toward the extreme position. It should be appreciated that the shell member 16 can be designed in many ways to vary the angular distance between planes P1 and P2, and that the liner 20 can be configured in accordance with the design of the shell member to obtain various minimum, maximum and intermediate angles for socket opening 60. It should also be appreciated that, depending on the locking mechanism utilized for liner 20, the liner can have an infinite or finite number of rotational positions. Where a frictional lock is utilized, for example, the liner 20 can have an infinite number of positions.

Stem component 14 is preferably made of a medical grade material, including metals such as chrome cobalt, suitable for implantation in the body and has a configuration and size in accordance with a bone in the body to which the stem component is to be affixed. Stem component 14 is particularly designed to replace the natural femoral head at the upper end of the femur or thigh bone and includes an elongate stem or shank 66 and a ball or head 68 coupled to stem 66 by a neck 70. Stem 66 can have various flared, tapered or non-flared, non-tapered configurations and sizes for being affixed to the upper end of the femur, and the stem can be affixed to the femur, such as in the medullary cavity, in many various ways including bone ingrowth processes with a press fit, cementing, impaction, mechanical fixation devices or a combination thereof. If desired, all or a portion of the outer or external surface of the stem can be textured, irregular, made porous or with interstices or beads to facilitate bone ingrowth processes. Ball or head 68 is preferably continuously smooth, highly polished and of low friction with a partial spherical configuration to be rotatably mounted in socket 62. Neck 70 has a cylindrical configuration with a circular cross-section having a diameter smaller than the diameter of head 68. The sizes and configurations of stem 66, head 68 and neck 70 can vary in accordance with the physiological and anatomical features of the patient, and many various diverse types of stem components or balls including the natural femoral head can be utilized with the socket component 12.

A tool for introducing shell member 16 at the joint being operated and positioning the shell member on a surface of a bone to which the socket component 12 is to be affixed is illustrated in FIG. 10 at 72. Introducer 72 includes a handle 74 for being grasped by a surgeon and a head or retaining member 76 coupled with handle 74 for retaining or holding shell member 16 upon the introducer. Handle 74 can have various configurations and sizes to facilitate grasping by a surgeon and to access the joint being operated. As illustrated in FIG. 10, handle 74 has an elongate T-shaped configuration including an elongate central cylindrical shank 78 and a cylindrical cross-piece 80 perpendicularly joined to an end of the shank with a longitudinal axis of the handle being coaxial with shank 78. A cylindrical collar 82 at an end of shank 78 opposite cross-piece 80 is received in a recess in retaining member 76 thereby coupling handle 74 with the retaining member. Retaining member 76 has a generally cylindrical forward portion 84 and a partial spherical end portion 86 joined to forward portion 84 at a circular junction 88. The forward and end portions 84 and 86 are of a size and configuration to be closely received in intermediate and end cavity sections 30 and 32, respectively, of cavity 18 of shell member 16 with the junctions 36 and 88 substantially aligned. Forward portion 84 has a length greater than the length of intermediate cavity section 30 to extend lengthwise from junction 88 to a planar forward wall 90 disposed forwardly of the rim 24 of shell member 16 when the retaining member 76 is received in the cavity 18. Forward wall 90 is contained in a plane perpendicular to the handle longitudinal axis, and the recess receiving collar 82 is concentrically disposed in the forward wall. Retaining member 76 has a longitudinal axis perpendicular with a plane containing junction 88, the retaining member longitudinal axis being angularly offset from the longitudinal axis of handle 74 by an angle that is the same as the angle between the longitudinal axis of cavity 18 and the longitudinal axis of shell 16. Various detent mechanisms, such as ball detent 92, can be provided to releasably retain the shell member 16 upon the retaining member 76. Ball detent 92 is disposed along the periphery of forward portion 84 of retaining member 76 to engage the wall of intermediate cavity section 30 and resist removal of shell member 16 from introducer 72.

Figure 12:
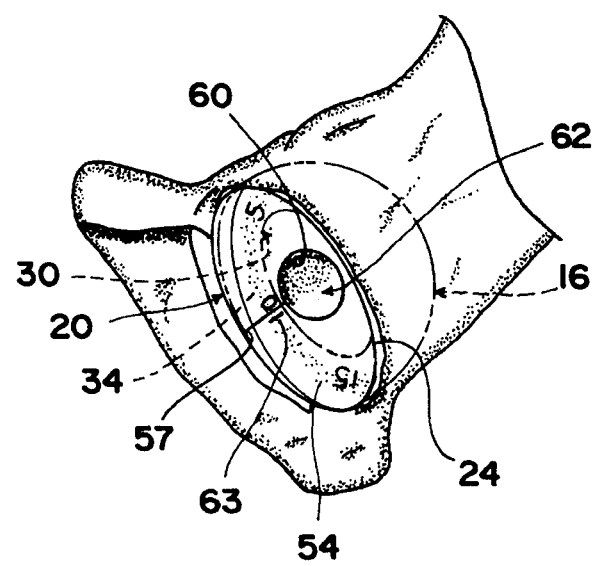
FIG. 12 is a perspective view of the socket component according to the present invention following implantation on the acetabular recess.

According to a method of operation for socket component 12 in hip surgery, the acetabulum and the upper end of the femur of a patient are prepared in accordance with well known surgical techniques to receive socket component 12 and femoral stem component 14, respectively. In most cases, the natural femoral head is removed and a cavity is prepared in the femur upper end to receive stem 66 of the stem component 14. Where possible, prosthetic stem component 14 may be eliminated allowing the natural bone structure of the femur to serve as the ball of the joint. The acetabulum is typically prepared by reaming to remove diseased or damaged tissue and form a hemispherical or partial spherical recess 23 for receiving shell member 16. Once the bone surfaces have been suitably prepared, trial socket and stem components are positioned on the prepared bone surfaces. Where a prosthetic stem component 5 is utilized to replace the natural femoral head, a trial stem component, such as one corresponding to stem component 14, best suited anatomically and physiologically to the patient is temporarily installed on the femur with the stem 66 of the stem component positioned in the prepared cavity. A trial socket component, such as one corresponding to socket component 12 best suited to the patient is selected by the surgeon, and the shell member 16 of the trial socket component as inserted in the prepared acetabular recess 23. When inserting trial shell member 16, the surgeon first determines the most desirable orientation for the shell member within or relative to the acetabular recess 23 to obtain a certain size or angle of overhang at a certain location to most advantageously orient the socket opening to prevent dislocation of the ball of stem component 14 therefrom. This determination is made in accordance with the anatomical and physiological features of the patient, and the indicia markings of the shell member 16 allow the surgeon to select a desired size or angle of overhang and to position the selected overhang where desired. Where it is desired to prevent dislocation of the head or ball posteriorly, for example, the surgeon determines the size of socket opening angle desired and then positions the indicia marking corresponding to the desired angle posteriorly along the acetabular recess at the desired location to resist dislocation. Dislocation of the joint anteriorly can be avoided by inserting the shell member 16 in the acetabular recess 23 with an indicia marking corresponding to a desired socket opening angle positioned anteriorly along the acetabular recess at the location desired to resist dislocation of the joint. Trial shell 16 can be inserted on the acetabulum in many various ways including via introducer 72 as will be explained further below. Once the trial shell 16 has been inserted as desired, a trial liner, such as one corresponding to liner 20, is inserted within the cavity 18 of the shell member. Once inserted, the liner 20 is dialed or rotated to align reference mark 57 with the indicia marking corresponding to the size of angle previously selected. With the ball of trial stem component 14 received in the socket 62 of the liner 20, the trial components are tested by moving the patient's leg. If it is discovered upon moving the patient's leg that there is a tendency toward dislocation of the joint, the liner 20 can be dialed or rotated to change the size of the angle and the version or orientation of socket opening 60 to avoid dislocation. Once the optimal position for the socket component has been determined via the trial procedure, the trial components are removed and final components are implanted. As illustrated in FIG. 11, shell member 16 of the final socket component 12 is placed on introducer 72 with the head or retaining member 76 of the introducer received in cavity 18 of the shell member and ball detent 92 resisting removal of the shell from the introducer. To facilitate proper assembly of shell member 16 on the retaining member 76, a positioning mark 94 can be provided on forward wall 90 for being aligned with second indicia marking 61. With the positioning mark 94 aligned with second indicia marking 61, the longitudinal axis of the handle 74 will be aligned with the longitudinal axis of the shell to allow insertion of shell 16 upon a bone surface utilizing conventional techniques. While grasping handle 74, the surgeon inserts the shell member 16 in the prepared acetabular recess 23 with a press fit. Shell member 16 is inserted in the acetabular recess 23 in a direction of insertion aligned with the longitudinal axis of handle 74 allowing the shell to be inserted straight into the acetabular recess. The final shell member 16 is inserted with the indicia marking corresponding to the desired size or angle for the socket opening positioned relative to the acetabular recess 23 as determined by the trial procedure, and the surgeon rotates or turns handle 74 to obtain the correct position of the shell member 16 for insertion. Shell member 16 is illustrated in FIG. 11 as being inserted in the acetabular recess 23 with indicia marking 63 located anteriorly of the acetabular recess as may be desirable when conducting surgery anteriorly. When positioning the selected indicia marking at the location or site desired, various anatomical landmarks as well as reference marks etched into the bone adjacent the acetabular recess can be utilized for alignment with the selected indicia marking. Depending on whether the selected indicia marking is to be positioned anteriorly or posteriorly, the left or right indicia markings can be utilized. Once the shell member 16 is properly inserted in the acetabular recess, introducer 72 is withdrawn. Where ball detent 92 is utilized, the shell member 16 can be held in place while the introducer is withdrawn with force sufficient to overcome the frictional lock of the ball detent. A final liner 20 is then inserted in the cavity 18 of the shell member 16, and the liner is rotated or dialed to align the reference mark 57 with the selected indicia marking as illustrated in FIG. 12 wherein the reference mark 57 is aligned with left indicia marking 63 corresponding to an angle of 10°. The liner 20 can be secured in shell member 16 with various diverse types of locking mechanisms. The head or ball of the stem component is then inserted in socket 62 and, if further adjustments are necessary to ensure stability of the joint, the liner 20 can be rotated or dialed to adjust the size of the angle and the orientation of the socket opening 60 to prevent dislocation. Where the maximum thickness of rear portion 50 is positioned posteriorly for increased coverage of the ball or head posteriorly, anteversion of the liner anteriorly due to a part of the forward portion 54 entering the cavity 18 permits increased motion toward the front of the joint. Where the maximum thickness of rear portion 50 is positioned anteriorly to resist dislocation of the joint anteriorly, retroversion of the liner posteriorly is increased to permit increased motion posteriorly.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A prosthetic socket component for articulating anatomical joints comprising:

a shell member for being secured to a first bone of the joint and having a longitudinal axis, a cavity and an opening communicating with said cavity, said shell member opening being disposed in a first plane perpendicular to said shell member longitudinal axis, said cavity having a longitudinal axis angularly offset from said shell member longitudinal axis; and a liner for being rotatably received in said cavity through said shell member opening and having a socket and an opening communicating with said socket, said shell member and said liner being configured to position said liner opening to protrude beyond said shell member opening such that said liner opening is disposed in a second plane disposed at an angle with said first plane when said liner is received in said cavity and to permit the size of said angle to be changed in response to rotation of said liner relative to said shell member about said cavity longitudinal axis.

2. A prosthetic socket component as recited in claim 1 wherein said shell member includes an outer surface for being affixed to the first bone of the joint, said outer surface terminating at a forward edge disposed in said first plane and circumscribing said shell member opening.

3. A prosthetic socket component for articulating anatomical joints comprising:

a shell member having an outer surface for being affixed to a first bone of the joint, a longitudinal axis, a cavity and an opening communicating with said cavity, said shell member opening being disposed in a first plane perpendicular to said shell member longitudinal axis, said outer surface terminating at a forward edge disposed in said first plane and circumscribing said shell member opening, said cavity having a longitudinal axis angularly offset from said shell member longitudinal axis; and a liner for being rotatably received in said cavity through said shell member opening and having a socket and an opening communicating with said socket, said shell member and said liner being configured to position said liner opening to protrude beyond said shell member opening such that said liner opening is disposed in a second plane disposed at an angle with said first plane when said liner is received in said cavity and to permit the size of said angle to be changed in response to rotation of said liner relative to said shell member about said cavity longitudinal axis, said cavity including a forward cavity section, an intermediate cavity section and an end cavity section, said shell member including a planar surface within said cavity and said forward cavity section having a length extending from said forward edge to said shell member planar surface, said shell member planar surface being contained in a third plane disposed at an acute angle with said first plane, said forward cavity section being tapered in accordance with said acute angle between said first plane and said third plane to have a maximum length and a minimum length.

4. A prosthetic socket component as recited in claim 3 wherein said liner includes a longitudinal axis, a mounting end for being received in said intermediate and end cavity sections and a hood joined to said mounting end and containing said liner opening, said hood having a portion for being received in said forward cavity section, said portion being tapered in accordance with the taper of said forward cavity section to have a maximum thickness corresponding to said maximum length and a minimum thickness corresponding to said minimum length.

5. A prosthetic socket component as recited in claim 4 wherein said liner is rotatable relative to said shell member between a neutral position wherein said maximum thickness is aligned with said maximum length and said second plane is disposed at a minimum angle with said first plane and an extreme position wherein said maximum thickness is aligned with said minimum length and said second plane is disposed at a maximum angle with said first plane.

6. A prosthetic socket component as recited in claim 5 and further including a reference mark on said liner and first and second indicia markings on said shell member for alignment with said reference mark in said neutral and extreme positions, respectively.

7. A prosthetic socket component as recited in claim 6 wherein said liner is rotatable relative to said shell member to a first intermediate position between said neutral and extreme positions wherein said second plane is disposed at a first intermediate angle with said first plane that is larger than said minimum angle and smaller than said maximum angle.

8. A prosthetic socket component as recited in claim 7 wherein said liner is rotatable relative to said shell member to a second intermediate position between said first intermediate position and said extreme position wherein said second plane is disposed at a second intermediate angle with said first plane that is larger than said first intermediate angle and smaller than said maximum angle.

9. A prosthetic socket component as recited in claim 8 and further including third and forth indicia markings on said shell member for alignment with reference mark in said first and second intermediate positions, respectively.

10. A prosthetic socket component for articulating anatomical joints comprising:

a shell member for being secured to a first bone of the joint and having a longitudinal axis, a cavity, a surface within said cavity and an opening communicating with said cavity, said opening being disposed in a first plane perpendicular to said shell member longitudinal axis, said shell member surface being disposed in a second plane disposed at an acute angle with said first plane; and a liner for being received in said cavity through said shell member opening and having a socket, an opening communicating with said socket and a surface for engaging said shell member surface, said shell member and said liner being configured to position said liner opening protrude angularly beyond said shell member opening such that said liner opening is disposed in a third plane disposed at an acute angle with said first plane when said liner surface is in engagement with said shell member surface and to permit said liner to be rotated relative to said shell member about an axis angularly offset from said shell member longitudinal axis to selectively change the size of said angle of said third plane with said first plane.

11. A prosthetic socket component as recited in claim 10 wherein said cavity includes a longitudinal axis, said liner includes a longitudinal axis, said liner longitudinal axis is aligned with said cavity longitudinal axis when said liner is received in said shell member and said liner is rotatable about said cavity longitudinal axis.

12. A prosthetic socket component as recited in claim 11 wherein said shell member includes an outer surface terminating at a forward rim disposed in said first plane and surrounding said shell member opening and said liner includes a rim to fit within said shell member rim.

13. A prosthetic socket component as for articulating anatomical joints comprising:

a shell member for being secured to a first bone of the joint and having a longitudinal axis, a cavity, an inner surface within said cavity and and opening communicating with said cavity, said opening disposed in a first plane perpendicular to said shell member longitudinal axis, said shell member inner surface being disposed in a second plane disposed at an acute angle with said first plane, said shell member including an outer surface terminating at a forward rim disposed in said first plane and surrounding said shell member opening; and a liner for being received in said cavity through said shell member opening and having a longitudinal axis, a socket, an opening communicating with said socket, a surface for engaging said shell member inner surface and a rim to fit within said shell member rim, said cavity including a longitudinal axis, said liner longitudinal axis being aligned with said cavity longitudinal axis when said liner is received in said shell member, said shell member and said liner being configured to position said liner opening to protrude angularly beyond said shell member opening such that said liner opening is disposed in a third plane disposed at an acute angle with said first plane when said liner surface is in engagement with said shell member inner surface and to permit said liner to be rotated relative to said shell member about said cavity longitudinal axis, said cavity longitudinal axis being angularly offset from said shell member longitudinal axis to selectively change the size of said angle of said third plane with said first plane, said liner being rotatable relative to said shell member between a neutral position wherein said third plane is positioned a predetermined minimum angular distance from said first plane and an extreme position wherein said third plane is positioned a maximum predetermined angular distance from said first plane.

14. A prosthetic socket component as recited in claim 13 wherein said liner rim is disposed substantially in said first plane in said neutral position.

15. A prosthetic socket component as recited in claim 14 wherein said liner rim is disposed in a fourth plane bisecting said first plane when said liner is in said extreme position.

16. A prosthetic socket component as recited in claim 15 wherein said liner includes a hood portion protruding beyond said first plane in said neutral position and part of said protruding portion enters said cavity when said liner is moved from said neutral position toward said extreme position.

17. A prosthetic socket component as recited in claim 16 wherein said part of said protruding portion that enters said cavity increases in size as said liner is moved from said neutral position toward said extreme position.

18. A prosthetic socket component as recited in claim 17 wherein said liner is rotatable 180° from said neutral position to said extreme position.

19. A prosthetic socket component as recited in claim 18 wherein said liner is rotatable approximately 60° from said neutral position to a first intermediate position wherein said third plane is positioned a first intermediate angular distance from said first plane.

20. A prosthetic socket component as recited in claim 19 wherein said liner is rotatable approximately 120° from said neutral position to a second intermediate position wherein said third plane is positioned a second intermediate angular distance from said first plane.

21. A prosthetic socket component as recited in claim 20 wherein said angular distance between said third plane and said first plane increases by increments of 5° as said liner is rotated from said neutral position to said first intermediate position, from said first intermediate position to said second intermediate position and from said second intermediate position to said extreme position.

22. A prosthetic hip joint comprising:

a ball member for being secured at the upper end of the femur;

a shell member for being secured to the acetabulum and having a longitudinal axis, a cavity and an opening communicating with said cavity, said opening being disposed in a first plane, said cavity having a longitudinal axis intersecting said first plane non-perpendicularly, said cavity longitudinal axis being angularly offset from said shell member longitudinal axis; and a liner rotatably received in said cavity through said shell member opening and having a portion protruding angularly beyond said shell member opening, a socket and an opening in said protruding portion communicating with said socket for receiving said ball member, said liner and said cavity being configured to permit the angular distance that said protruding portion protrudes beyond said cavity opening to be selectively changed in response to rotation of said liner relative to said shell member about said cavity longitudinal axis to selectively position said liner opening relative to said ball member without removal of said liner from said shell member.

23. A prosthetic hip joint comprising:

a ball member for being secured at the upper end of the femur;

a shell member for being secured to the acetabulum and having a cavity, an opening communicating with said cavity and a forward edge circumscribing said shell member opening, said shell member opening being disposed in a first plane, said cavity including a forward cavity section, an intermediate cavity section and an end cavity section; and a liner for being rotatably received in said cavity through said shell member opening and having a portion for angularly protruding beyond said shell member opening, a socket, an opening in said protruding portion communicating with said socket for receiving said ball member, a mounting end for being received in said intermediate and end cavity sections and a hood having a rear portion for being received in said forward cavity section, said protruding portion extending forwardly from said rear portion of said hood, said liner and said cavity being configured to permit the angular distance that said protruding portion protrudes beyond said cavity opening to be selectively changed in response to rotation of said liner relative to said shell member to selectively position said liner opening relative to said ball member without removal of said liner from said shell member.

24. A prosthetic hip joint as recited in claim 23 wherein said protruding portion is joined to said rear portion at a rim contained in a second plane and said liner opening is contained in a third plane disposed at an acute angle with said second plane.

25. A prosthetic hip joint as recited in claim 24 wherein said rim is substantially aligned with said forward edge in a neutral position wherein said angular distance corresponds to the angle between said third plane and said first plane.

26. A prosthetic hip joint as recited in claim 25 wherein said forward cavity section extends from said first plane to a platform within said cavity, said platform being contained in a fourth plane disposed at an acute angle with said first plane, said liner being rotatable relative to said shell member about an axis perpendicular to said fourth plane to change the angular distance that said protruding portion protrudes beyond said cavity opening.

27. A prosthetic hip joint as recited in claim 26 wherein said third plane in said neutral position is disposed at an angle of 5° with said first plane.

28. A prosthetic hip joint as recited in claim 27 wherein said fourth plane is disposed at an angle of approximately 7½° with said first plane.

* * * * *